United States Patent [19]

Gutierrez et al.

[11] 4,239,633

[45] Dec. 16, 1980

[54] MOLYBDENUM COMPLEXES OF ASHLESS POLYOL ESTER DISPERSANTS AS FRICTION-REDUCING ANTIWEAR ADDITIVES FOR LUBRICATING OILS

[75] Inventors: Antonio Gutierrez, Mercerville; Stanley J. Brois, Westfield, both of N.J.

[73] Assignee: Exxon Research & Engineering Co., Florham Park, N.J.

[21] Appl. No.: 45,066

[22] Filed: Jun. 4, 1979

[51] Int. Cl.$^3$ .............................................. C10M 1/48
[52] U.S. Cl. .............................. 252/32.7 E; 252/46.3; 252/46.7; 252/49.7; 260/429 R; 542/413; 542/427
[58] Field of Search ................ 252/32.7 E, 46.7, 49.7, 252/46.3; 542/413, 427; 260/429 R

[56] References Cited

U.S. PATENT DOCUMENTS

| | | | |
|---|---|---|---|
| 2,279,688 | 4/1942 | Larsen | 252/34 |
| 2,568,876 | 9/1951 | White et al. | 252/51.5 A X |
| 2,795,552 | 6/1957 | Abbott et al. | 252/49.7 |
| 2,805,997 | 9/1957 | Benoit, Jr. et al. | 252/42.7 |
| 2,948,747 | 8/1960 | Karbum et al. | 252/49.7 X |
| 2,987,478 | 6/1961 | Matson | 252/46.4 |
| 3,121,059 | 2/1964 | DeYoung et al. | 252/49.7 X |
| 3,172,892 | 3/1965 | LeSuer et al. | 252/51.5 A X |
| 3,219,666 | 11/1965 | Norman et al. | 252/51.5 A X |
| 3,223,625 | 12/1965 | Cyphers et al. | 252/18 |
| 3,272,746 | 9/1966 | LeSuer et al. | 252/47.5 |
| 3,381,022 | 4/1968 | LeSuer | 252/32.7 E X |
| 3,652,616 | 3/1972 | Watson et al. | 252/49.7 X |
| 3,755,173 | 8/1973 | Kennedy et al. | 252/54.6 |
| 4,017,406 | 4/1977 | Brois et al. | 252/51.5 A |

FOREIGN PATENT DOCUMENTS 967838  8/1964  United Kingdom .................... 252/49.7

*Primary Examiner*—Andrew Metz
*Attorney, Agent, or Firm*—R. A. Dexter; John J. Mahon

[57] ABSTRACT

An oil-soluble molybdenum complex of an ashless polyol ester dispersant, preferably of oil-soluble reaction product of a molybdenum compound such as molybdic acid with about 1 to 2 molar equivalents of a polyol ester of a hydrocarbon substituted diacid material such as polybutenyl succinic anhydride or a thio-bis-(hydrocarbyl substituted diacid material), such as thio-bis-(polyalkyl lactone acid) and/or their precursors, the adducts of sulfur chloride and unsaturated diacid materials, e.g., 4,8-bis-polyalkyl-4,8-dichloro-6-thiaundecane-1,2,10,11-tetracarboxylic acid bis-anhydride and their dehydrochlorinated analogs, is a useful additive to a lubricating oil since both the sludge dispersant and antifriction properties of said oil are enhanced.

5 Claims, No Drawings

MOLYBDENUM COMPLEXES OF ASHLESS POLYOL ESTER DISPERSANTS AS FRICTION-REDUCING ANTIWEAR ADDITIVES FOR LUBRICATING OILS

BACKGROUND OF THE INVENTION

The present invention concerns oil-soluble molybdenum complexes of polyol ester dispersants, their method of preparation, and the utility of oil-soluble molybdenum polyol ester dispersants as lubricating oil additives, which markedly improve the friction-reducing properties of lubricating oils employed for crankcase lubrication of internal combustion engines.

There are two principle environments which are encountered by automotive crankcase lubricants, i.e. cyclical high and low temperatures from stop-and-go driving and continuous high temperatures from extended operation of the automobile over long distances. Each of these environments provokes the presence in the lubricant of varying proportions of foreign particles such as dirt, soot, water and decomposition products resulting from breakdown of the oil. This foreign matter appears responsible for the deposition of a mayonnaise-like sludge which circulates with the oil.

During the past decade, ashless sludge dispersants have become increasingly important, primarily in improving the performance of lubricants in keeping the engine clean of deposits and permitting extended crankcase oil drain periods while avoiding the undesirable environmental impact of the earlier used metal-containing additives. One commercial type of ashless dispersant involves esters of alkenyl substituted acids, e.g. polyisobutenyl succinic acids, with polyols e.g., pentaerythritol, as taught in U.S. Pat. No. 3,381,022; however, such dispersants often-times contain olefinic unsaturation making them susceptible to oxidative degradation especially under high severity conditions such as elevated oil temperatures and extended drain intervals.

A second type of ester dispersant involves chloro lactone ester dispersants prepared via the esterification of alkenyl chloro lactone acids with pentaerythritol as taught in U.S. Pat. No. 3,755,173; however, the inherent propensity of such dispersants, or antirust compounds as taught in U.S. Pat. No. 2,279,688 towards elimination of corrosive HCl to give unsaturated products, can promote decomposition of the hydrocarbon lubricant, corrode metal engine parts, and promoter varnish deposition on the internal surfaces of the engine.

In the operation of an internal combustion engine, there are many "Boundary Lubrication" conditions where two rubbing surfaces must be lubricated, or otherwise protected, so as to prevent wear and to insure continued movement. Moreover, where, as in most cases, friction between the two surfaces will increase the power required to effect movement and where the movement is an integral part of an energy conversion system, it is most desirable to effect the lubrication in a manner which will minimize this friction and/or reduce wear. As is also well known, both wear and friction can be reduced, with various degrees of success, through the addition of a suitable additive or combination thereof, to a natural or synthetic lubricant. Similarly, continued movement can be insured, again with varying degrees of success, through the addition of one or more appropriate additives.

While there are many known lubricant additives which may be classified as antiwear, antifriction and extreme pressure agents and some may in fact satisfy more than one of these functions as well as provide other useful functions but rarely if ever dispersancy, it is also known that many of these additives act in a different physical or chemical manner and often compete with one another, e.g. they may compete for the surface of the moving metal parts which are subjected to lubrication. Accordingly, extreme care must be exercised in the selection of these additives to insure compatibility and effectiveness.

Known ways to solve the problem of energy losses due to high friction in crankcase lubrication include the use of synthetic ester base oils which are expensive and the use of insoluble molybdenum sulfide and graphite dispersions which have the disadvantage of giving the oil composition a black or hazy appearance. It would be desirable then to provide oil-soluble molybdenum compounds and thus overcome the disadvantage. Oil-soluble molybdenum additives taught as useful in lubricating oils include: colloidal molybdenum complexes in combination with dispersants (see U.S. Pat. No. 3,223,625); the reaction product of molybdenum ions and hydrocarbon-substituted succinic anhydride-alkylene polyamines carried out in oil and a cosolvent such as water, tetrahydrofuran and dimethylformamide (see U.S. Pat. No. 3,652,616); and oil-soluble molybdenum containing succinimides (see translation of Khimiya i Teknologuja Topliv i Masel, No. 6 pp 49–51 of June 1978 having article entitled "Antioxidant Efficiency and Mechanism of Antioxidant Action of Metal-Containing Dispersant Additives").

The practical exploitation of various types of molybdenum compounds and complexes as lubricant additives has been hindred not only by their insolubility and/or corrosiveness but also by their synthetic accessibility.

While it is known that molybdenum compounds can be reacted with low molecular weight aliphatic alcohols or glycols (see U.K. Pat. No. 967,838) and with alcohols (see U.S. Pat. Nos. 2,805,997 and 2,987,478), it would be desirable to design molybdenum complexes of high molecular weight polyol ester dispersants to enhance the lubricity of oils and fuels to which said esters are added.

It is an object of this invention to overcome the related disadvantages and shortcomings of the prior art materials.

SUMMARY OF THE INVENTION

It has now been discovered that ashless polyol ester dispersants under suitable reaction conditions can be converted into molybdenum-containing ester dispersants having the property of imparting enhanced lubricity to lubricating oils particularly when said oil contains an oil-soluble active sulfur donor. An operational embodiment of the invention thus is a lubricating oil composition comprising a major proportion of mineral oil and a minor but at friction-reducing amount of an oil-soluble molybdenum-containing ashless polyol ester lubricating oil dispersant, said dispersant having from 0.5 to 20 wt.% molybdenum based on the weight of said dispersant and further characterized by ester functionality and a substantially saturated hydrocarbon group containing at least about 50 carbon atoms.

These materials are prepared from polyol ester dispersants by reaction of said dispersant with a molybdenum source compound such as molybdic acid, in a binary solvent system comprising dimethyl formamide and a hydrocarbon such as a neutral oil, e.g. Solvent 150 Neutral. The volume ratio of dimethyl formamide to hydrocarbon ranges from 1:10 to 10:1, preferably 1:4 to 2:1, optimally 1:1.

It has now been further discovered that a stable molybdenum complex can be obtained with little if any destruction of the ashless dispersant when complexing is effected at a temperature of 40° C. to 250° C., preferably from 50° to 200° C., in said binary solvent system.

In accordance with the present invention, it is preferred that the lubricity enhancing, i.e. friction-reducing, additive is present in the mineral oil in an amount to provide from about 0.01 to 2.0, preferably 0.02–1.0 and optimally 0.05–0.5 weight percent molybdenum in said oil, most usefully containing in addition at least 0.25 weight percent of an oil-soluble active sulfur donor. All weight percent values are based on the total weight of the lubricating composition.

In a preferred non-thio form, the molybdenum complex is that of a polyol ester dispersant additive derived from the reaction of one mole of a $C_8$ to $C_{400}$ hydrocarbyl substituted dicarboxylic acid material such as polyisobutenyl succinic anhydride or the corresponding $C_8$ to $C_{400}$ hydrocarbyl substituted lactone acid such as polyisobutyl lactone acid as taught in U.S. Pat. No. 4,123,373. Preferable hydrocarbyl substituents include polyisobutenyl groups with $\overline{M}_n$ ranging from about 700 to 5,600, optimally from about 900 to 1600 with from one to two, preferably 1.0 to 1.5, molar equivalents of a polyhydric alcohol having a total of 2 to about 100 carbon atoms and represented by the formula:

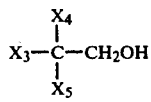

wherein: $X_3$ is hydrogen, $C_1$ to $C_5$ alkyl, hydroxy, hydroxy alkyl $HO(CH_2)_n$ wherein n is 1–10, hydroxyalkoxy $HO(CH_2CH_2O)_nCH_2CH_2O$, wherein n is 1–40 and hydroxyalkylthio $HO\text{-}(CH_2CH_2S)_nCH_2CH_2O$ wherein n is 1 to 10; and $X_4$ and $X_5$ may be the same or different and represent hydrogen, $C_1$ to $C_5$ alkyl and $C_1$ to $C_5$ hydroxyalkyl groups and their ester, ether, acetal or ketal derivatives.

Esterification is achieved by heating at a temperature of from 140° C. to 240° C. until cessation of water evolution; said additive being complexed with from 0.1 to 1 molar equivalents of molybdic acid and containing from about 0.05 to 10, preferably about 0.2 to 5, optimally about 4 wt.% molybdenum, which corresponds to a ca 2:1 molar ratio of ester dispersant to molybdenum.

In a preferred thio form, the molybdenum complex is that of a polyol ester dispersant additive represented by the formula:

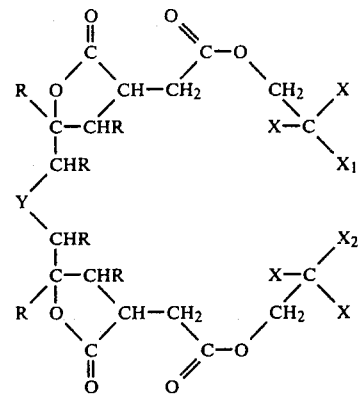

wherein R is selected from the group consisting of hydrogen, hydrocarbyl and substituted hydrocarbyl containing from 1 to 10,000 carbons with the restriction that at least one R has at least about 4 carbons; Y is selected from the group consisting of S (thio), S—S (dithio), S=O (sulfinyl), $SO_2$ (sulfonyl), Se (seleno), $S$—$(CH_2)_zS$— where z is a number of from 2 to 10, X, $X_1$ and $X_2$ are selected from the group consisting of hydrogen, alkyl, hydroxyl, acyloxy, hydroxyalkyl, $CH_2OCH_2C(CH_2OH)_3$, and —$O(CH_2$—$CH_2O)_nH$ where n is 1 to 50 and preferably at least one X group contains a hydroxy moiety, and that typically $X_1$ and $X_2$ are hydrogen bonded so as to form a macrocyclic-like configuration. In some cases, depending on stoichiometry, the nature of the reactants, and the mode of synthesis, $X_1$ and $X_2$ together can represent a linking group such as O, S, S—S, N-alkyl, —$CH_2OCH_2$, —$CH_2OCH_2$—$C(CH_2OH)_2$—$CH_2OCH_2$—, —$O(CH_2C\text{-}H_2O)_n$—, wherein n is 1–50; such linking groups create equimolar (i.e., one mole of thio bis-(acylating agent) to one mole of polyol (1:1) macrocyclic ring structures of varying sizes and composition depending upon the nature of the thio-bis-(acylating reagent) and the polyhydric alcohol. Sometimes, $X_1$ and $X_2$ may bond to another molecule of thio-bis-(acylating agent) e.g. thio-bis-(lactone acid) in which instance, two acylating reactants essentially combine with two polyols (2:2) to yield structurally larger macrocyclic esters of doubled molecular weight. Furthermore, equimolar ester products of thio-bis-(acylating agent) and polyol are capable of forming, under suitable reaction conditions, ever larger macrocyclic structures, e.g. (3:3), (4:4), etc. Usually, mixtures of linear and cyclic ester oligomers are formed, and the ratio of cyclic to linear oligomers is a sensitive function of reaction conditions, and the nature of the reactants; however, with a judicious choice of experimental conditions, one can achieve a suitable mix of cyclic and linear esters for specific end uses.

DETAILED DESCRIPTION OF THE INVENTION

In the following description of this invention, the reactants, i.e., the acylating agents or the thio-bis-acylating agents, their formation via the bridging (or coupling) of alkene diacid materials with a sulfur halide or a sulfur halide equivalent such as a sulfenate ester-HCl combination reagent or a thiol-halogen combination reagent; the esterification reactions of the acylating agents or the bridged plating reagents, complexing with molybdenum compounds and utilization of the novel products are set forth below in detail.

ALKENE DIACID MATERIALS

The alkene diacid materials also known as the acylating agent is a hydrocarbyl substituted dicarboxylic acid material, i.e., acid or anhydride or ester and includes alpha-beta unsaturated $C_4$ to $C_{10}$ dicarboxylic acid, or anhydrides or esters thereof, such as fumaric acid, itaconic acid, maleic acid, maleic anhydride, chloromaleic acid, dimethyl fumarate, etc., which are substituted with a hydrocarbyl group, usefully a hydrocarbon chain containing from 8 to 400 carbons (branched or unbranched) and includes long hydrocarbon chains of more than 50 carbons generally an olefin polymer chain, when useful oil-solubility is required.

In general, these hydrocarbyl substituted dicarboxylic acid materials and their preparation are well known in the art, for example, see U.S. Pat. Nos. 3,219,666; 3,172,892; 3,272,746; the aforementioned prior art patents; as well as being commercially available, e.g., polyisobutenyl succinic anhydride.

The dicarboxylic acid material can be illustrated by an alkenyl substituted anhydride which may contain a single alkenyl radical or a mixture of alkenyl radicals variously bonded to the cyclic succinic anhydride group with the alkenyl substituent containing from 8 to 400 carbons and preferably from 50 to 300 carbons. The anhydrides can be obtained by well-known methods, such as the Ene reaction between an olefin and maleic anhydride or halo-succinic anhydride or succinic ester (U.S. Pat. No. 2,568,876).

Suitable olefins include octene, decene, dodecene, tetradecene, hexadecane, octadecene, eicosene, and polymers of propylene, butene, isobutene, pentene, decene and the like, and halogen-containing olefins. The olefins may also contain cycloalkyl and aromatic groups.

With 2-chloromaleic anhydride and related acylating agents, alkenylmaleic anhydride reactants are formed.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of: ethylene and propylene; butylene and isobutylene; propylene and isobutylene; etc. Other copolymers include those in which a minor amount of the copolymer monomers, e.g., 1 to 20 mole % is a $C_4$ to $C_{18}$ non-conjugated diolefin, e.g., a copolymer of isobutylene and butadiene; or a copolymer of ethylene, propylene and 1,4-hexadiene; etc.

The olefin polymers will usually have $(\overline{M}_n)$s within the range of about 700 and about 6,000, more usually between about 900 and about 5,600. Particularly useful olefin polymers have $(\overline{M}_n)$s of about 1200 to 5000 with approximately one terminal double bond per polymer chain. An especially valuable starting material for a highly potent dispersant additive are polyalkenes e.g., polyisobutylene, having about 90 carbons.

THIO-BIS-(ACYLATING REAGENTS)

The preparation of the mono- or dithio-bis-(lactone alkanoic acid or ester), mono- or dithio-bis-(alkene dioic acid or anhydride or ester) or dithio-bis-(alkane dioic acid or anhydride or ester) acylating agents involve the sulfur halide coupling or bis-sulfenyl halide-induced coupling of the oxidative coupling of $H_2S$ or thioacid adducts of the alkene diacid materials. The alkene diacid materials are understood to comprise such structures in their anhydride form as:

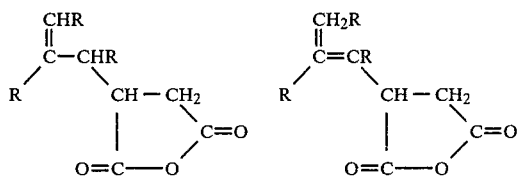

with the $\gamma,\delta$-unsaturated isomers predominating and wherein R may be hydrogen or hydrocarbyl or substituted hydrocarbyl containing from 1 to about 10,000 and more carbons with the restriction that at least one R has at least 1 carbon, preferably from about 16 to about 400 carbons and optimally from about 60 to about 100 carbons. Many of these hydrocarbyl substituted dicarboxylic acid materials and their preparation are well known in the art as well as being commercially available, e.g. 2-octadecenyl succinic anhydride and polyisobutenyl succinic anhydride. With 2-chloromaleic anhydride and related acylating agents, alkenylmaleic anhydride reactants are formed. Bridging of these products with $YCl_2$ affords another viable approach to thio-bis-(acylating reagents).

As taught in U.S. patent application Ser. No. 954,051 filed Oct. 23, 1978, the bridging or coupling of the precursor acylating agents can be achieved via a number of synthetic options including (i) i.e. the above-noted addition of sulfur halides or bis-sulfenyl halides or alkyl sulfenate/HCl reagent to unsaturated diacids, hemi-esters, diesters or anhydrides, (ii) the oxidative coupling of unsaturated acids previously thiylated with $H_2S$ or $R_1C(=O)SH$, where $R_1$ represents a $C_1$-$C_5$ alkyl group, or (iii) reaction of $\alpha,\omega$-alkane-dithiols, $H_2S$, or a suitable thiylating agent, with epoxidized or halogenated alkene dioci acid or anhydride materials.

The preferred pathway to bridged acylating agents involves the reaction of sulfur halides, bis-sulfenyl halides or a sulfenate ester-HCl reagent with unsaturated diacids, hemi-esters, di-esters or anhydrides in the temperature range of $-60°$ C. to about $100°$ C., optimally from about $10°$ C. to $50°$ C. If desired, solvents comprising hydrocarbons such as pentane, hexane, heptane, cyclohexane, mineral oil; halocarbons such as methylene chloride, chloroform, carbon tetrachloride, aromatics such as toluene, chlorobenzenes, xylene; ethers, such as diethyl ether and tetrahydrofuran (THF); and, acids such as acetic, propionic and trifluoroacetic acid, can be used in favorably controlling viscosity and reaction temperature. The mode of addition of reagents is dictated by convenience. Usually, the sulfur halide is added dropwise to an unsaturated diacid, ester, or acid anhydride, preferably diluted in an inert diluent. With reactive diluents, namely those containing unsaturates including aromatics, and olefins such as polyisobutylene, sufficient sulfur halide must be added to effect complete bridging of the olefin diacid reactants.

The addition of one mole of sulfenyl halide to 2 moles of alkene dioic acid anhydride at low temperatures, e.g. $-60°$ C. to about $20°$ C., affords a discrete $YCl_2$-anhydride adduct [A] which upon treatment with water or simple alcohol, i.e., $R_1OH$ where $R_1$ can be hydrogen, methyl, ethyl or isopropyl in the presence of acid catalyst (e.g. $H_2SO_4$, Amberlyst 15, etc.) engenders the lactone acid A and/or ester B,

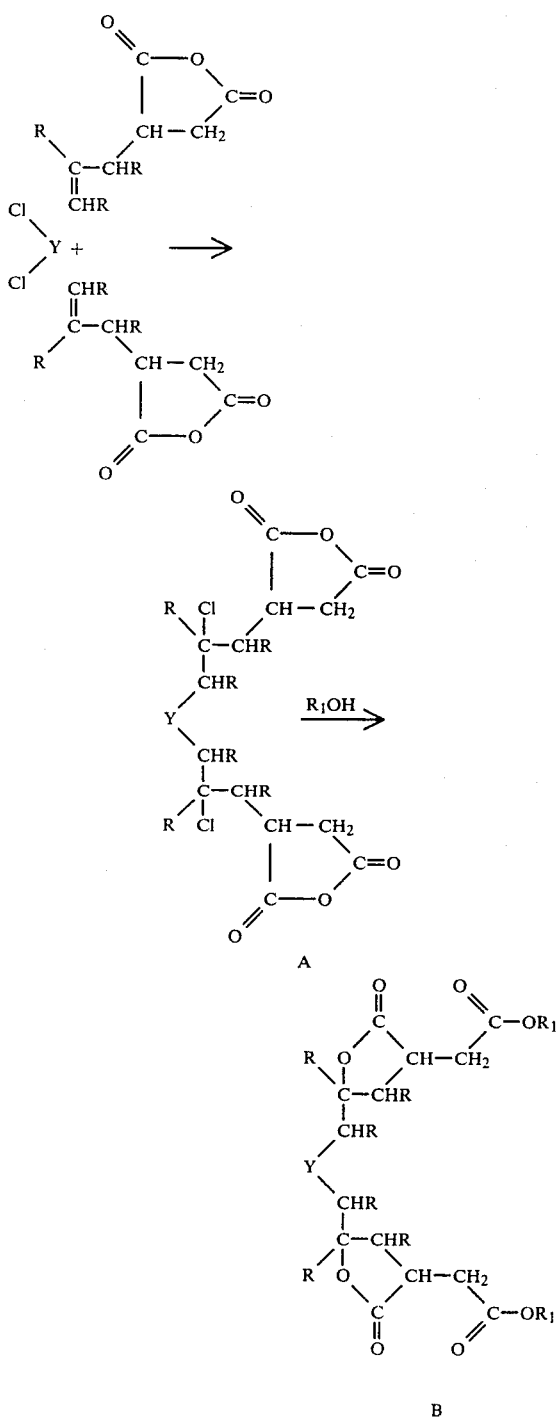

with R and Y being the same as previously defined.

Both reactants A and B can be esterified with polyols such as pentaerythritol to give the desired sulfur-bridged polyol ester products. The bridging and esterification processes are fully described in U.S. patent application Ser. No. 954,051 filed Oct. 23, 1978 of common assignee which is incorporated herein by reference hereto.

POLYOL REACTANTS

The polyhydric alcohols used in esterifying the acylating reagents, i.e. both the alkene diacid materials and the thio-bis-(acylating reagents) can have a total of 2 to about 100 carbon atoms and can be represented by the formula:

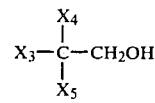

wherein: $X_3$ is hydrogen, $C_1$ to $C_5$ alkyl, hydroxyl, hydroxyalkyl $HO(CH_2)_n$ wherein n is 1–10, hydroxyalkoxy $HO(CH_2CH_2O)_n$—, wherein n is 1–40, hydroxyalkylthio $HOCH_2CH_2S(CH_2CH_2S)_n$—, wherein n is 1 to 10; and hydroxyalkylamino $HO(CH_2CH_2NCH_3)_n$—, wherein n is 1 to 10; and $X_4$ and $X_5$ may be the same or different and represent hydrogen, $C_1$ to $C_5$ alkyl and $C_1$ to $C_5$ hydroxyalkyl groups and their ester, ether, acetal or ketal derivatives.

Examples of useful acetals and ketals include mono- and bis-formals of pentaerythritol; mono- and bis-acetal and benzal analogs of pentearythritol; and the cyclic formal and acetal of $HO(CH_2CH_2O)_nH$ wherein n is 4–8.

Examples of useful glycol and polyethylene glycol reactants include ethylene glycol, diethylene glycol, tetraethylene glycol, dipropylene glycol, tripropylene glycol, dibutylene glycol, tributylene glycol, and other alkylene glycols in which the alkylene group contains from two to about eight carbon atoms. Other useful polyhydric alcohols include glycerol, monooleate of glycerol, monostearate of glycerol, monomethyl ether of glycerol, 9,10-dihydroxy stearic acid, methyl ester of 9,10-dihydroxy stearic acid, 1,2-butanediol, 2,3-hexanediol, 2,4-hexanediol, pinacol, erythritol, arabitol, 1,2-cyclohexanediol, and xylene glycol. Carbohydrates such as sugars, starches, celluloses, etc., likewise may yield the ester reactants of this invention. The carbohydrates may be exemplified by glucose, fructose, sucrose, rhamnose, mannose, glyceraldehyde, and galactose.

An especially preferred class of polyhydric alcohols are typified by pentaerythritol, dipentaerythritol, tripentaerythritol, polypentaerythritols, sorbitol, mannitol, cyclohexaamylose, cycloheptaamylose and related polyhydric alcohols such as these prepared via the aldol condensation of formaldehyde with ketones such as acetone, and cyclohexanone, e.g. 2,2,6,6-tetramethylol-1-cyclohexanol.

ESTERIFICATION CONDITIONS

The esters may be readily prepared by one of several methods including, if desired, the esterification in the presence of a catalyst. The method which is preferred can be effected by adding from 0.2 to 5, preferably 1–2 moles of the aforesaid polyol per mole of the acylating reagent with or without an inert diluent, and heating the mixture at 100°–240° C., preferably 170°–220° C. until reaction is complete by infrared analysis of the product showing maximal absorption for ester.

The water formed as a by-product is removed by distillation as the esterification proceeds. A solvent may be used in the esterification to facilitate mixing and temperature control. It also facilitates the removal of water from the reaction mixture. The useful solvents which are inert solvents in the above reaction include hydrocarbon oils, e.g. mineral lubricating oil, kerosene, neutral mineral oils, xylene, halogenated hydrocarbons, e.g., carbon tetrachloride, dichlorobenzene, tetrahydrofuran, etc.

In some instances, it is advantageous to carry out the esterification in the presence of a catalyst such as sulfuric acid, Amberlyst 15 (sulfonated polystyrene) benzene sulfonic acid, p-toluene sulfonic acid, phosphoric acid, etc. The amount of the catalyst in the reaction may be as little as 0.01% (by weight of the reaction mixture), more often from about 0.1% to about 5%.

The relative proportions of the acylating reagent and the polyhydroxy reactant which are to be used depend to a large measure upon the type of the product desired and the number of hydroxyl groups present in the molecule of the hydroxy reactant. For instance, the formation of an ester of the thio-bis (alkyl lactone acid), i.e., one in which each acid radical is esterified, involves the use of two moles of the polyol for each mole of thio-bis (acylating reagent).

MOLYBDENUM SOURCE

Useful molybdenum reagents include oxo-compounds of molybdenum-(V) and -(VI) which are capable of complexing with the polyol ester dispersant to provide thermally stable molybdenum complexes containing from about 0.5 to 20, preferably 2 to 10, optimally about 5 wt.% molybdenum based on the total weight of said complex. The sources of molybdenum include molybdenum trioxide ($MoO_3$), molybdic acid, ammonium molybdate, ammonium paramolybdate, and molybdenum halides, such as $MoCl_5$ or $MoO_2Cl_2$.

METHOD OF PREPARING THE COMPLEX

The molybdenum-polyol ester complex is substantially the product of a reaction between 1-3 moles of the polyol ester dispersant and about 1 mole of a suitable molybdating reagent such as molybdic acid. The reaction is readily carried at an elevated temperature of from 40° C. to 250° C., preferably 50° C. to 200° C., optimally 150° C. to 180° C., usually in the presence of an organic nitrogen base. In accord with the instant invention, it has been found that organic nitrogen bases particularly N,N-dialkylamides function as effective catalysts in the formation of glycol molybdates via the reaction of polyol ester dispersants with molybdic acid or related molybdenum reagents. While other non-reactive nitrogen bases are sometimes operative, e.g. trisubstituted amines such as diazabicyclooctane, N-ethyl morpholine, etc., N,N-dialkylamides, comprising dimethylformamide (DMF), dimethylacetamide, N-methyl-2-pyrrolidone and hexamethyl phosphoramide are preferred. The complex-forming reaction is conveniently effected at a temperature in the range of from about 150° to 180° C. in a neutral oil such as Solvent 150 Neutral, containing the nitrogen base catalyst. The concentration of catalyst can be in the range of from 10 to about 200 weight percent, the preferred range being from about 20 to 100 percent based on the polyol ester dispersant employed. Only minor amounts of molybdenum can be incorporated into the polyol dispersant without the nitrogen base catalyst.

It is preferred that the mole ratio of polyol ester dispersant to molybdic acid (or equivalent) be within the range of from 2 to 1, preferably 2.

The complexing reaction is easily carried out over a period of from about 0.25 to 20, preferably 0.5 to 6, hours in order to suitably stabilize the complex. The nitrogen base catalyst, e.g. dimethyl formamide, is generally removed by distillation, e.g., stripping with nitrogen, and complex dissolved in mineral oil for ease of handling if the latter was not used as a cosolvent.

Carrying out the organo molybdenum complexing reaction in the dimethylformamide solvent system provides benefits over reaction without dimethyl formamide or in light aromatic solvent such as toluene or a light hydrocarbon oil, e.g. mineral oil or in the presence of water including: completion of reaction to a stabilized molybdenum complex; faster reaction time at a lower temperature; and, an additive product solution which when added to lubricating oil provides both enhanced friction reduction and sludge dispersancy activities to the lubricating oil.

SULFUR DONORS

The hydrocarbon-soluble molybdenum complexes of the polyol dispersants provide not only dispersancy for lubricating oils but enhanced lubricity as well in said oils when used in combination with an active sulfur donor which can be defined as a compound which when used in admixture with the dispersant-molybdenum complex reduces the coefficient of friction at least about 10% relative to that provided by the complex alone. The active sulfur donor is present in an amount of from about 0.1 to 10, preferably 0.2 to 2, parts by weight per part by weight of molybdenum complex.

Illustrative of active sulfur donors are metal dihydrocarbyl dithiophosphates and the corresponding precursor esters, phosphosulfurized pinenes, sulfurized olefins and hydrocarbons, sulfurized fatty esters and sulfurized alkyl phenols.

Preferred are the zinc dihydrocarbyl dithiophosphates which are salts of dihydrocarbyl esters of dithiophosphoric acids and may be represented by the following formula:

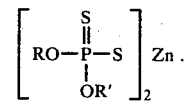

wherein R and R' may be the same or different hydrocarbyl radicals containing from 1 to 18 and preferably 2 to 12 carbon atoms and including radicals such as alkyl, alkenyl, aryl, aralkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, tert-butyl, amyl n-hexyl, i-hexyl, n-heptyl, n-octyl decyl, dodecyl, octadecyl, 2-ethylhexyl, phenyl, butylphenyl, cyclohexyl, methylcyclopentyl, propenyl, butenyl, etc. In order to obtain oil solubility, the total number of carbon atoms in the dithiophosphoric acid will average about 5 or greater.

The zinc dihydrocarbyl dithiophosphates which are useful as the coadditive, i.e. sulfur donor, of the present invention may be prepared in accordance with known techniques by first esterifying a dithiophosphoric acid usually by reaction of an alcohol or phenol with $P_2S_5$ and then neutralizing the dithiophosphoric acid ester with a suitable zinc compound such as zinc oxide.

In general, the zinc dihydrocarbyl dithiophosphate will be used in the lubricating composition at a concentration within the range of about 0.01 to about 5 parts by weight per 100 parts of lubricating oil and preferably from about 0.5 to about 1.5. This is adequate for sulfur donation whereby the lubricity enhancement of the lubricating oil composition by the coadditive combination is markedly realized.

As noted earlier, an equally suitable active sulfur donor is the dihydrocarbyl esters of dithiophosphoric acid which may be represented by the formula:

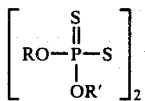

where R and R' are as previously defined. Particularly useful is the dibutylphenyl dithiophosphate.

The phosphorosulfurized terpenes as represented by pinene, dipenene, allo-ocimene, etc., are another group of dithiophosphate diesters which are active sulfur donors. Of the terpenes, the bicyclic pinene is preferred. The phosphosulfurized terpene is readily obtained by reaction of about one mole of diester of thiophosphoric acid and one mole of pinene at a temperature of at least 100° C., e.g. 100° C. to 200° C. The preferred active sulfur donor can be characterized as the bornyl ester of dihydrocarbyl ($C_2$-$C_{20}$) dithiophosphoric acids (as shown in U.S. Pat. No. 2,689,258).

The sulfurized olefins and hydrocarbons are further esters of thiophosphoric acids which are useful sulfur donors. These esters are achieved by reaction with olefins such as ethylene, propylene, isobutylene, decene, dodecene, octadecene, etc., olefin polymers of molecular weight ranging from 100 to 50,000 such as ethylene, propylene, isobutylene, etc., aromatics such as benzene, napthylene, toluene, xylene, etc., petroleum fractions and condensation products of halogenated aliphatic hydrocarbons with aromatic compounds, e.g. wax naphthalene (see U.S. Pat. No. 2,804,431).

The sulfurized fatty esters are another subclass of esters which are active sulfur donors. These products are readily obtained from the reaction of $P_2S_5$ and aliphatic alcohols usefully having from about 8 to 22 carbons obtained from natural sources including linoleic, palmolitic, behenic, stearic, palmitic, lauric, capric, etc., as well as mixtures obtained from vegetable and animal oils such as tall oil.

The sulfurized alkyl phenols are generally $C_4$ to $C_{20}$ alkyl phenol sulfides. These sulfurized alkyl phenols are readily produced by sulfurizing an alkyl phenol with a sulfur halide or elemental sulfur.

OTHER ADDITIVES FOR LUBRICATING COMPOSITIONS

In addition to the molybdenum complex of the polyol ester dispersant and active sulfur donor, the lubricating oil composition may contain other well-known lubricating oil additives to provide trouble-free operation of the lubricated equipment, such as ashless dispersants, metallic detergents, supplemental oxidation and corrosion inhibitors, extreme pressure agents, rust inhibitors, pour point depressants, viscosity index improvers, etc.

1. ASHLESS DISPERSANTS

As used herein, the terminology "ashless dispersant" in describing both the reactant and the additive is intended to describe the now well-known class of non-metal-containing oil-soluble polymeric additives or the acyl derivatives of relatively high molecular weight carboxylic acids which are capable of dispersing contaminants and the like in hydrocarbons such as lubricating oils. The carboxylic acids may be mono- or polycarboxylic acids and they are generally characterized by substantially hydrocarbon constituents containing an average of 50 to 250 aliphatic carbon atoms.

A preferred class of ashless dispersants are the nitrogen-containing dispersant additives which are generally known in the art as sludge dispersants for crankcase motor oils. These dispersants include mineral oil-soluble salts, amides, imides and esters made from high molecular weight mono- and dicarboxylic acids (and where they exist the corresponding acid anhydrides) and various amines of nitrogen-containing materials having amino nitrogen or heterocyclic nitrogen and at least one amido or hydroxy group capable of salt, amide, imide or ester formation. Usually, these dispersants are made by condensing a monocarboxylic acid or a dicarboxylic acid or anhydride, preferably a succinic acid producing material such as alkenyl succinic anhydride, with an amine or alkylene polyamine. Usually, the molar ratio of acid or anhydride to amine is between 1:1 to 5:1, e.g. 2 mole of $C_{10}$-$C_{100}$ polyisobutenyl succinic anhydride to 1 moles of tetraethylene pentamine.

Paimarily because of its ready availability and low cost, the hydrocarbon portion of the mono-, or dicarboxylic acid or anhydride is preferably derived from a polymer of a $C_2$ to $C_5$ monoolefin, said polymer generally having between 50 and 250 carbon atoms. A particularly preferred polymer is polyisobutylene.

Polyalkyleneamines are usually used to make the non-metal-containing dispersant. These polyalkyleneamines include those represented by the general formula:

wherein n is 2 to 3 and m is a number from 0 to 10. Specific compounds coming within the formula include diethylenetriamine, tetraethylenepentamine, dipropylenetriamine, octaethylenenonamine, and tetrapropylenepentamine; N,N-di-(2-aminoethyl) ethylenediamine may also be used. Other aliphatic polyamino compounds that may be used are N-amino-alkylpiperazines, e.g. N-(2-aminoethyl)piperazine. Mixtures of alkylene polyamines approximating tetraethylene pentamine are commercially available, e.g. Dow E-100 sold by Dow Chemical Company of Midland, Michigan.

Representative dispersants are formed by reacting about one molar amount of polyisobutenyl succinic anhydride with from about one to about 0.5 molar amounts of tetraethylene pentamine or with from about 0.5 to 1.5 moles of a polyol, e.g. pentaerythritol.

It is possible to modify the ashless dispersants generally by the addition of boron, for example, in order to enhance the performance of the additive. This is readily accomplished by adding boric acid to the reaction mixture after the imidation or esterification is substantially complete and heating the mixture at temperatures of 100° to 150° C. for a few hours.

Detergents useful in conjunction with dispersants, preferably the ashless type, include normal, basic or over-based metal, e.g. calcium, magnesium, etc., salts of petroleum naphthenic acids, petroleum sulfonic acids, alkyl benzene sulfonic acids, oil-soluble fatty acids, alkyl salicyclic acids, alkylene-bis-phenols, and hydrolyzed phosphorosulfurized polyolefins.

Oxidation inhibitors include hindered phenols, e.g. 2,6-ditert. butyl para-cresol, amines, sulfurized phenols and alkyl phenothiazines.

Pour point depressants include wax alkylated aromatic hydrocarbons, olefin polymers and copolymers, acrylate and methacrylate polymers and copolymers.

Viscosity Index Improvers include olefin polymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl pyrrolidone or dimethylaminoalkyl methacrylate, post-grafted polymers of ethylene-propylene with an active monomer such as maleic anhydride which may be further reacted with an alcohol or an alkylene polyamine, styrene/maleic anhydride polymers post-treated with alcohols and amines, etc.

Rust inhibition activity can be provided by the aforementioned oil-soluble active sulfur donors such as the metal dihydrocarbyl dithiophosphates and the corresponding precursor esters phosphosulfurized pinenes, sulfurized olefins and hydrocarbons, sulfurized fatty esters and sulfurized alkyl phenols. Preferred are the zinc dihydrocarbyl dithiophosphates which are salts of dihydrocarbyl esters of dithiophosphoric acids.

Although a wide variety of lubricating oils may be improved by the molybdate complex ester dispersants of the invention, they are most effective in mineral oils having a viscosity as measured by ASTM D-445 of from about 2 to 40, preferably 5 to 20, centistokes at 99° C.

If the molybdenum-containing ester dispersant is used as an additive concentrate, the concentrate may consist essentially of from about 5 to 80 weight percent of molybdenum containing dispersant, based on the total weight of said concentrate, the remainder being a suitable solvent such as kerosene, mineral oil, synthetic oil and a naphtha or the like. The preferred concentrate contains about 10-60 weight percent of the additive combination in the solvent.

Whether the molybdated ester dispersant is used alone or in combination with other additives, its concentration may vary appreciably with the particular application. For example, when the said molybdenum containing dispersants are used alone in a fuel such as gasoline, the concentration of the additive ranges from 1 to 1000, preferably 5–50 parts per million, based on the total weight of the gasoline. In a lubricant, however, it is used from about 0.1 to 20, preferably 0.5–5% based on the total weight of the oil.

The invention will be further understood by reference to the following Examples which illustrate a preferred form of the invention and compares the same with different, though similar compositions.

The following Examples illustrate more clearly the compositions of the present invention. However, these illustrations are not to be interpreted as specific limitations on this invention.

EXAMPLE 1

About 300 g of a mineral oil solution containing 50% by weight of a pentaerythritol polyalkenyl succinate ester derived from the reaction of one mole of pentaerythritol with one mole of polyisobutenyl succinic anhydride, said polyisobutenyl substituent having a $\overline{M}_n$ of 980, were dissolved in 100 ml of dimethylformamide (DMF) and mixed with 60 g of molybdic acid. The reaction slurry was heated to the refluxing temperature of DMF (145°–150° C.). After heating for about one hour, a clear, dark blue solution was obtained. It turned dark green after 12 hours of refluxing. The DMF was nitrogen stripped off by heating at 150° C. for 2 hours, and the resulting oil solution was filtered hot. The clear, green oil solution featured a kinematic viscosity of 582 SSU at 210° F., and a hydroxyl number of 20.7. It analyzed for 1.98% Mo. Its infrared spectrum showed an absence of hydroxyl absorption bands indicating that most of the free hydroxyl groups had reacted with the molybdic acid to form a molybdate glycol ester complex. The starting polyol ester dispersant reactant showed an infrared spectrum with a strong hydroxyl absorption band, and featured a kinematic viscosity of 1283 SSU at 210° F., and a hydroxyl number of 70.5.

EXAMPLE 2

About 100 g of pentaerythritol polyisobutenylsuccinic acid ester dispersant as a 50 wt.% solution in Solvent 150 Neutral, prepared via reaction of equimolar amounts of polyisobutenyl succinic anhydride of $\overline{M}_n \approx 1400$, and pentaerythritol were dissolved in 100 ml of DMF, and mixed with 10 g of molybdic acid. Heating the reaction mixture to reflux at 145°–150° C. for 1½ hrs. afforded a dark blue-greenish solution. The DMF solvent was distilled off and the residue was dissolved in 1 liter of pentane. The pentane solution was washed five times with 200 ml aliquots of water, dried over magnesium sulfate and filtered. Rotoevaporation of the dried pentane solution at 100° C. under high vacuum for several hours gave a green oil which analyzed for 1.75% Mo.

EXAMPLE 3

One-hundred grams of a commercial dispersant, identified as Lz 936 and sold by the Lubrizol Corp. of Cleveland, Ohio and believed to be a 50 wt.% solution of polyisobutenyl succinate ester of pentaerythritol, were dissolved in 100 ml of DMF and stirred with 10 g of 85% molybdic acid. The reaction mixture was heated to reflux for 6 hours. A deep blue solution was obtained. The product was diluted in one liter of pentane and washed five times with 200 ml of water. The pentane solution was dried over magnesium sulfate, filtered, and rotoevaporated under high vacuum at 100° C. The resulting dark, blue oil solution featured an infrared spectrum devoid of any hydroxyl absorption band and analyzed for 3.46 wt.% Mo.

EXAMPLE 4

Approximately 130 g of polyisobutenyl succinic acid of $\overline{M}_n \approx 776$, prepared via hydrolysis of PIBSA and having a Sap. No. of ca 84 were dissolved in 400 ml of chloroform. The olefin diacid reagent was sulfenylated via the dropwise addition of 0.05 mole (5.3 g) of $SCl_2$ to the stirred solution. After refluxing the mixture overnight, two drops of sulfuric acid were added, the solvent was stripped off, and the mixture heated at about 100° C. overnight. The product featured an infrared spectrum with strong lactone and acid carbonyl absorption bands in the 5.6–5.85 micron region and analyzed for 1.69% sulfur and 0.09% chlorine, and is hereinafter designated thio-bis-(polyisobutyl lactone acid).

Approximately 0.01 mole (26.3 g) of the thio-bis-(polyisobutyl lactone acid) prepared as described above and 0.02 mole (2.8 g) of pentaerythritol were mixed and heated to 200° C. for about 2 hours. (Ester formation was monitored by IR analysis). The product was diluted with an equal weight of Solvent 150 Neutral oil and filtered. The infrared spectrum of the filtrate featured characteristic absorption bands at 2.9–3.0 microns (hydroxyl) and a broad band in the 5.65–5.8 micron region (lactone ester). The hydroxyl number for the product solution (50 wt.%) was found to be 83. The product showed a GPC peak maximum at $M_n \approx 7000$ and is believed to be a mineral oil solution of bis-pentaerythritol ester of thio-bis-(polyisobutyl lactone acid.

About 150 g of the thio-bis-polyisobutyl lactone ester of pentaerythritol prepared as above were mixed with 60 g of molybdic acid in 200 ml of dimethylformamide (DMF), and 150 g of mineral oil, and then heated to reflux for 4 hrs.

The DMF catalyst was distilled from the blue-green solution by rotoevaporation at 150° C. for several hours. The filtered oil solution featured an infrared spectrum with dominant ester and lactone carbonyl absorption bands, virtually no hydroxyl absorption band; and analyzed for 1.36% molybdenum.

EXAMPLE 5

The following Examples 5a and 5b show that complexing does not occur when the reaction is carried out in the absence of dimethylformamide and in binary solvent systems of toluene-water and xylene-water, respectively.

5(a)

About 100 g of the pentaerythritol ester of polyisobutenylsuccinic anhydride (said polyisobutenyl group having a $\overline{M}_n$ of 1400) were dissolved in 100 ml of xylene and mixed with 10 g of water, and 4 g of molybdic acid. The reaction mixture was refluxed for 10 hours and then filtered. Removal of xylene by distillation afforded a residue which analyzed for 0.02 wt.% Mo.

5(b)

About 100 g of the bis-pentaerythritol ester of thio-bis-(polyisobutenylsuccinic anhydride) was prepared by reacting one mole of thio-bis (polyisobutenylsuccinic anhydride) with 2 moles of pentaerythritol at 210–215 for 3 hrs. were admixed with 100 ml of toluene and 10 cc of water. The reaction mixture was stirred at room temperature and treated with 4 g of molybdic acid. Then, the slurry was refluxed for ten hours. At the end of the tenth hours, the product mixture was filtered and the toluene was distilled off. The residue analyzed for 0.16 wt.% Mo.

In both 5(a) and 5(b) only trace amounts of molybdenum were incorporated into the polyol ester dispersant.

EXAMPLE 6

The molybdated dispersants of Examples 1–4 were evaluated, in a formulated oil, for its effect on friction in a Roxana Four-Ball Tester. As a comparative example, an oil containing the dispersant but without molybdenum was run. The concentration of the molybdenum-containing dispersant was adjusted to provide 0.1% molybdenum in the oil. A total dispersant concentration of 2.5% was maintained in all tests.

The lubricant composition was:

| Component | Wt % Active Ingredient |
| --- | --- |
| Dispersant | 2.5 |
| Magnesium Sulfonate (overbased) | 0.4 |
| Zinc dinonyl phenoxy | 1.0 |

| Component | Wt % Active Ingredient |
| --- | --- |
| dithiophosphate | |
| Mineral oil | 96.1 |

The Roxana Four-ball wear tester with the Brown/GE modification from Roxana Machine Works, St. Louis, MO was used to measure friction properties by the following procedure. The tester were assembled in the normal wear procedure as described in ASTM D2266-67 using four ½″ bearing steel balls. The tester was brought to 110° C. and run at 1200 rpm and 15 kg for a minimum of 45 minutes. If the frictional force as seen on the strip chart recorder is constant for the last 10 minutes, the speed is reduced to 25 rpm. Otherwise, the test is carried on until frictional force has stabilized. The test at 25 rpm is carried out at 110° C. and 15 kg for 15 minutes or until frictional force has stabilized.

The representative compounds of the invention were evaluated by subjecting the products of Examples 1–4 to a study of each one's utility as a lubricity enhancing and/or antiwear additive for lubricating oils by using said Testing Procedure.

The results of tests under said Testing Procedure A are set forth in Table I.

From the foregoing, it is shown that the molybdenum-containing ester dispersant additives of the invention provide lubricity enhancement to lubricating oils.

It is to be understood that the Examples present in the foregoing specification are merely illustrative of this invention and are not intended to limit it in any manner; nor is the invention to be limited by any theory regarding its operability. The scope of the invention is to be determined by the appended claims.

TABLE 1
COMPARISON OF MOLYBDENUM CONTAINING DISPERSANTS FOR FRICTION REDUCTION

| Test # | Molybdate Product of Example # | Coefficient of Friction[1] 1200 rpm | 50 rpm | Friction Reduction[2] 1200 rpm | 50 rpm |
| --- | --- | --- | --- | --- | --- |
| 6-1 | 1 | 0.051 | 0.053 | 45 | 52 |
| 6-2 | 2 | 0.053 | 0.057 | 43 | 47 |
| 6-3 | 3 | 0.048 | 0.080 | 48 | 26 |
| 6-4 | 4 | 0.054 | 0.072 | 41 | 27 |
| 6-5 | — | 0.093 | 0.108 | — | — |

[1] 15 kg load
[2] Relative to base oil reported as Ex. 6-5

What is claimed is:

1. A lubricating oil composition comprising a major proportion of mineral oil and a minor but friction-reducing amount of an oil-soluble molybdenum complex of a polyol ester lubricating oil dispersant, said dispersant having from 0.5 to 10 wt.% molybdenum based on the weight of said dispersant, said polyol ester being the reaction product of a $C_2$–$C_{100}$ polyhydric alcohol with either (a) a $C_8$–$C_{400}$ hydrocarbyl substituted $C_4$–$C_{10}$ dicarboxylic acid, anhydride or ester or (b) a mono- or dithio-bis-(lactone alkanoic acid anhydride ester), mono- or dithio-bis-(alkene dioic acid or anhydride or ester) or dithio-bis-(alkane dioic acid, anhydride or ester) acylating agent, said agent containing a hydrocarbyl or substituted hydrocarbyl group having from 1 to about 10,000 carbon atoms.

2. A lubricating oil composition according to claim 1 further comprising an oil-soluble active sulfur donor selected from the group consisting of metal dihydrocarbyl dithiophosphates and the corresponding precursor esters thereof, phosphosulfurized pinenes, sulfurized olefins and hydrocarbons, sulfurized fatty esters and sulfurized alkyl phenols, said composition providing from about 0.01 to 2.0 weight percent molybdenum and said sulfur donor being present in at least 0.25 weight percent, all of said weight percents being based on the total weight of said composition.

3. A composition according to claim 1 wherein said complex is oil-soluble and derived from the reaction product of one mole of a hydrocarbyl substituted dicarboxylic acid material wherein said hydrocarbyl substituent has a ($\overline{M}_n$) ranging from 700 to 5,000 reacted with one to two moles of a polyhydric alcohol having a total of 2 to about 100 carbon atoms and represented by the formula:

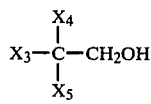

wherein: $X_3$ is hydrogen, $C_1$ to $C_5$ alkyl, hydroxy, hydroxy alkyl $HO(CH_2)_n$ wherein n is 1–10, hydroxyalkyl $HO(CH_2CH_2O)_nCH_2CH_2O$, wherein n is 1–40 and hydroxyalkylthio alkoxy, $HO\text{-}(CH_2CH_2S)_nCH_2CH_2O$ wherein n is 1 to 10; and $X_4$ and $X_5$ may be the same or different and represent hydrogen, $C_1$ to $C_5$ alkyl, and $C_1$ to $C_5$ hydroxyalkyl groups and their ester, ether, acetal or ketal derivatives.

4. A composition according to claim 1 wherein said mineral oil has a viscosity as measured by ASTM D-445 of from about 2 to 40 centistokes at 99° C., said polyol ester dispersant is polyisobutenyl succinic anhydride wherein said polyisobutenyl group has a ($\overline{M}_n$) ranging from 900 to 1600, and reacted with from 1.0 to 1.5 moles of said polyhydric alcohol, said polyhydric alcohol being pentaerythritol and said mineral oil further comprising zinc dihydrocarbyl dithiophosphate as the sulfur donor present in an amount of from 0.2 to 2 parts by weight per part by weight of said molybdenum complex which is present in an amount of from 0.02 to 1.0 wt.% based upon the total weight of said composition.

5. A concentrate comprising from 5 to 80 wt.% of the combination of an oil-soluble molybdenum complex of a polyol ester dispersant, the polyol ester being the reaction product of a $C_2$-$C_{100}$ polyhydric alcohol and either (a) a $C_8$-$C_{100}$ hydrocarbyl substituted $C_4$-$C_{10}$ dicarboxylic acid, anhydride or ester or (b) a mono- or di-thio-bis-(lactone alkanoic acid anhydride or ester), mono- or dithio-bis-(alkene dioic acid or anhydride or ester), or dithio-bis-(alkane dioic acid or anhydride or ester) acylating agent, said agent containing a hydrocarbyl or substituted hydrocarbyl group having from about 1 to 10,000 carbon atoms, said complex having from 0.5 to 10 wt.% molybdenum based on the weight of said dispersant and from about 0.1 to 10 parts by weight of active sulfur donor per part by weight of said complex, said sulfur donor being a member of the group consisting of metal dihydrocarbyl dithiophosphates and the corresponding precursor esters thereof, phosphosulfurized pinenes, sulfurized olefins and hydrocarbons, sulfurized fatty esters and sulfurized alkyl phenols, and 20 to 95 wt.% of an additive concentrate solvent selected from the group consisting of kerosene, mineral oil, synthetic oil or naphtha.

* * * * *